United States Patent
Cailleteau

[19]

[11] Patent Number: 5,946,738
[45] Date of Patent: Sep. 7, 1999

[54] SUPPLE POUCH INCORPORATING SLEEVE FOR OPENING

[76] Inventor: Benoît Cailleteau, 97 avenue du Prado, 13006 Marseille, France

[21] Appl. No.: 08/984,854

[22] Filed: Dec. 4, 1997

[30] Foreign Application Priority Data

Dec. 12, 1996 [EP] European Pat. Off. .............. 96402711

[51] Int. Cl.⁶ .................................................... A47K 11/00
[52] U.S. Cl. ............................................. 4/144.1; 4/144.3
[58] Field of Search .................................. 4/144.1, 144.3, 4/144.2, 144.4; 604/349, 350, 329; 383/43, 44

[56] References Cited

U.S. PATENT DOCUMENTS 3,746,240  7/1973  Flynn ........................................ 4/144.3
5,065,459  11/1991  Tjahaja et al. .
5,745,926  5/1998  Cailleteau ................................. 4/144.1

FOREIGN PATENT DOCUMENTS 0748620  12/1996  European Pat. Off. .
513827  3/1930  Germany .

*Primary Examiner*—David J. Walczak
*Attorney, Agent, or Firm*—Ostrolenk, Faber, Gerb & Soffen, LLP

[57] ABSTRACT

A pouch presenting a supple outer envelope having an open collar followed by a widened part. The pouch has a reinforcing element having a relatively rigid and flexible sleeve extending in the collar from a first end located in the vicinity of the opening of the collar, up to a second end located towards the widened part. The sleeve presents, in the vicinity of the base of the collar, a cut-out on either side of which are defined a first portion and a second portion. The second portion is provided with two substantially traverse tabs which face each other and which have free lateral ends. In the flattened configuration of the pouch in which the opening is closed, the sleeve is itself flattened and presents two wall elements disposed one against the other, while, in order to bring the collar into its substantially tubular configuration and open the opening, the sleeve is capable of being elastically deformed in order to adapt a so-called "open" configuration, in which the first portion is substantially tubular, while the lateral ends of the tabs are spaced apart from one another.

11 Claims, 5 Drawing Sheets

SUPPLE POUCH INCORPORATING SLEEVE FOR OPENING

FIELD OF THE INVENTION

The present invention relates to a bag or pouch presenting a supple outer envelope, comprising a collar followed by a widened part, the collar having a free end defining an opening, the pouch being capable of adopting a flattened configuration in which the opening is closed, while the collar is capable of adopting a substantially tubular configuration in which the opening is open, the pouch further being provided with a reinforcing element disposed at least in the vicinity of the free end of the collar.

BACKGROUND OF THE INVENTION

Bags or pouches of this type are used for receiving waste in generally liquid form, particularly waste of human origin such as urine or vomit. Such pouches are normally in their flattened form and are opened to receive the waste. On that occasion, the pouch is held in the vicinity of the free end of the collar to oblige the latter to adopt its substantially tubular configuration. Once the waste has been introduced, it suffices to release the free end of the collar so that it naturally resumes its flattened configuration, thus closing the opening.

Such pouches are currently made with thin sheets of paper or of plastics material, possibly transparent, endowed with the desired suppleness. For opening, the reinforcing element is deformed by the user, which obliges that part of the collar disposed around this element, to adopt the desired tubular configuration.

The transverse dimensions of the opening are chosen to suit the use which it is desired to make of the pouch. Generally, especially when the pouch is intended to receive urine or vomit, the opening must be able to be manipulated with one hand, with the result that its transverse dimensions are clearly smaller than the current transverse dimensions of the pouch. For example, when the pouch is used as urinal, its maximum width and that of the opening may vary respectively between 15 and 20 cm and between 4 and 10 cm, depending on whether the user is an adult or a child.

The presence of the reinforcing element makes it possible to open the opening of the upper end of the collar by bringing together the two longitudinal edges of this element which determine its maximum width in the flattened configuration. However, due to the suppleness of the material which constitutes the outer envelope of the pouch, there is a risk that only the collar is suitably opened, while the rest of the outer envelope remains flat, the sheets which constitute this envelope naturally tending to remain "stuck" to one another. Consequently, when the pouch is being used, there is a risk of reflux towards the outside for the product poured in the pouch.

It is an object of the present invention to overcome this drawback by proposing a pouch or bag for which the passage of the collar to the tubular configuration ensures spacing apart of the walls of the outer envelope not only in the region of this collar, but also at least in the region of the widened part near the collar.

SUMMARY OF THE INVENTION

This object is attained thanks to the fact that the reinforcing element is constituted by a relatively rigid and flexible sleeve disposed inside the pouch, this sleeve extending in the collar from a first end located in the vicinity of the opening, up to a second end located towards the widened part; the sleeve presents, in the vicinity of the base of the collar joined to the widened part, a cut-out on either side of which are defined a first portion located towards the first end of the sleeve and a second portion located towards the second end of said sleeve, the second portion being provided with at least two substantially transverse tabs which face each other and which have free lateral ends; and, in the flattened configuration of the pouch, the sleeve is itself flattened and presents two wall elements disposed one against the other, while, in order to bring the collar into its substantially tubular configuration and open the opening, the sleeve is capable of being elastically deformed in order to adapt a so-called "open" configuration, in which the first portion is substantially tubular, while the lateral ends of the tabs are spaced apart from one another.

It will be understood that, thanks to this conformation, the deformation of the sleeve makes it possible not only to take the collar to its diameter of opening thanks to the first portion of the sleeve, but also to space apart the walls of the pouch at least in the widened part of its outer envelope due to the spacing apart of the tabs with which the second portion of the sleeve is equipped.

The qualification of the sleeve as being "relatively rigid and flexible" is understood to mean that it is made of a material presenting a rigidity greater than that of the outer wall of the pouch. For example, the sleeve may be made of light cardboard or a plastic whose thickness is greater than that of the plastic constituting the outer wall.

According to a particularly advatangeous embodiment, the sleeve comprises a member for maintaining in open configuration, capable of being actuated to maintain said sleeve in its open conformation.

This maintaining member, for example formed by a tongue arranged in a zone of fold of the sleeve, is particularly advantageous when the pouch is intended to serve as urinal for women, since it avoids any untimely closure of the pouch even if, due to a wrong manipulation, the pressure of the hand placing the sleeve in its open configuration is inadvertently released.

BRIEF DESCRIPTION OF THE DRAWINGS

The invention will be more readily understood on reading the following description with reference to the accompanying drawings, in which.

DESCRIPTION OF PREFERRED EMBODIMENTS

Figure 1:
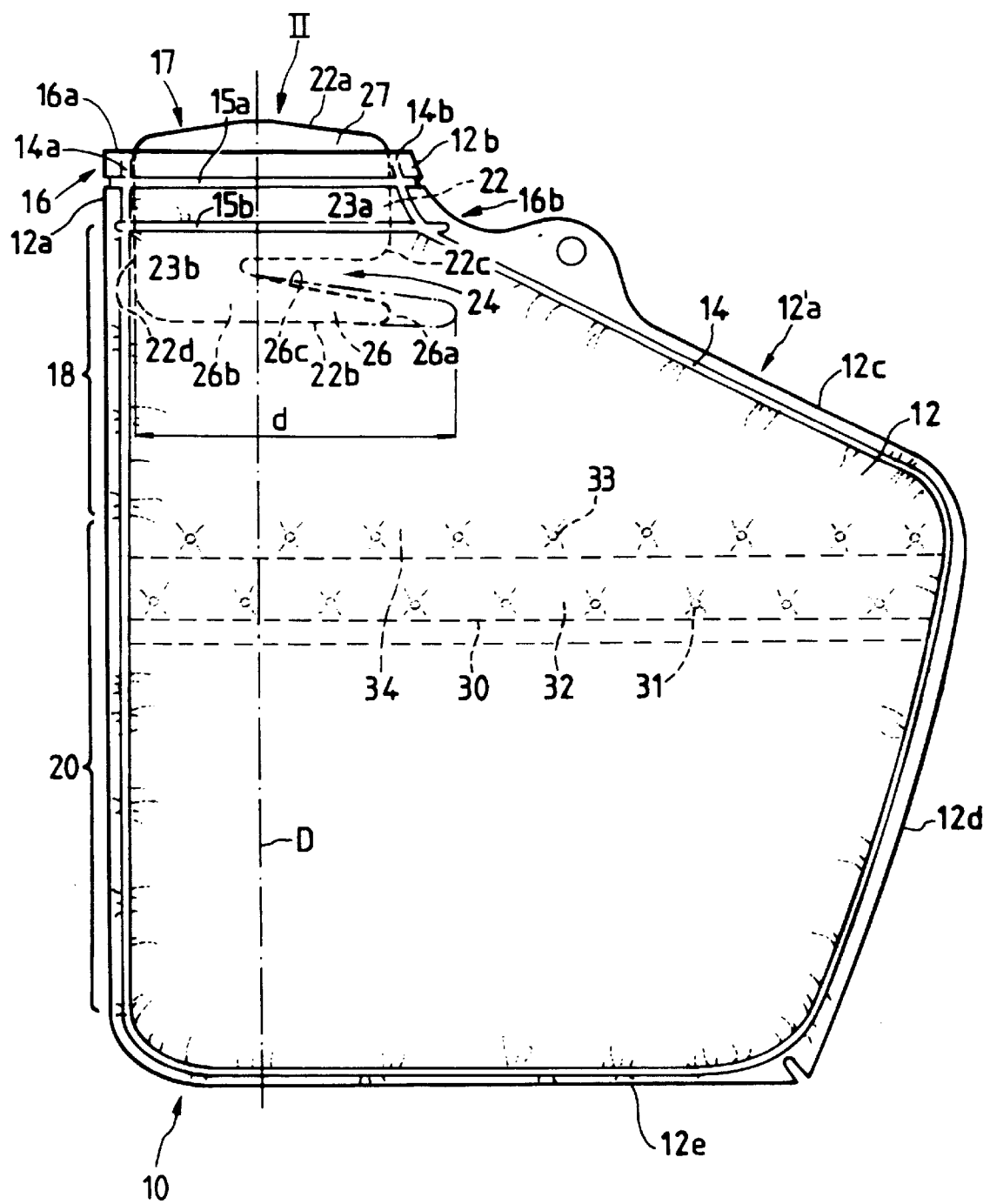
FIG. 1 is a view in elevation of a pouch according to the invention, in its flattened configuration.
Figure 1A:
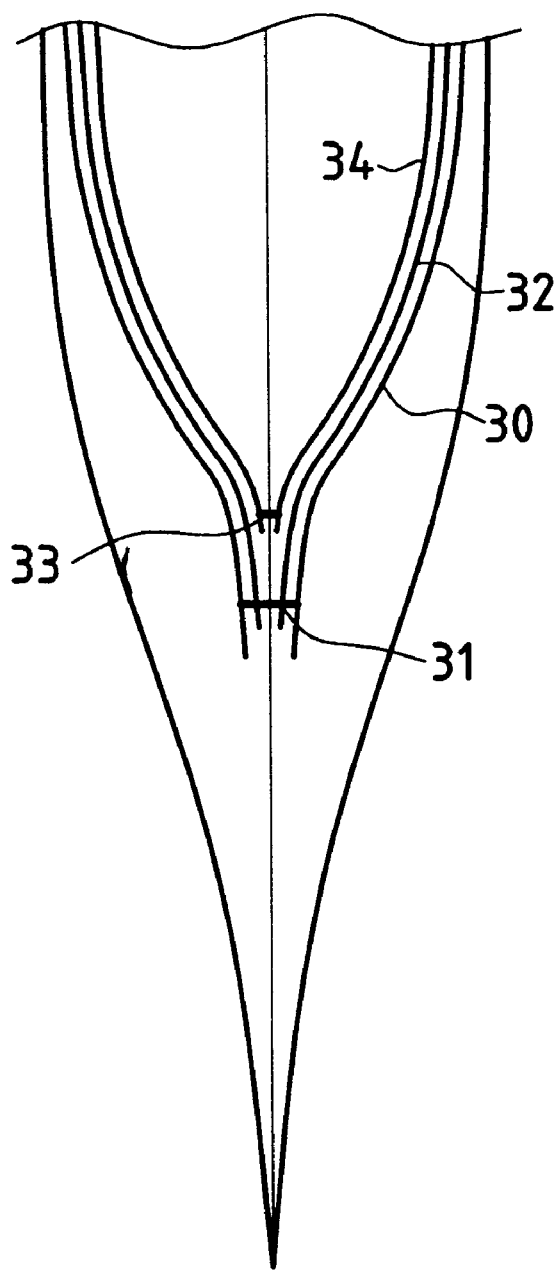
FIG. 1A is diagrammatic longitudinal section of the pouch of FIG. 1, showing a part of said pouch.

Referring now to the drawings, FIG. 1 shows a safety pouch 10, for example intended to be used as urinal. This pouch comprises an outer envelope 12 which is supple. This envelope is for example made from two thin sheets of plastics material, suitably cut out and welded on each other over virtually the whole contour, by a line of weld 14.

The envelope 12 comprises a collar 16 which, going towards the bottom of the pouch, is followed by a widened part 18, itself followed by a useful part 20 of the pouch which presents a substantially constant width.

More precisely, in the example shown, an edge 12a of the envelope 12 is substantially rectilinear from the free end of the collar 16, while the opposite edge 12'a firstly presents a first portion 12b which is located in the region of the collar 16 and which is substantially parallel to the edge 12a in this region, or which at the most tends to move slightly apart from this edge 12a. The edge 12'a then presents a second portion 12c which moves away from edge 12a. It is this portion 12c which defines the widened portion 18 of the outer envelope. Finally, the useful part 20 of the pouch is defined between the edge 12a and the portion 12d of the edge 12'a which faces it. This portion 12d may be substantially parallel to edge 12a or, as in the example shown, may have a slight tendency to move towards it. Other configurations are possible, the essential being to obtain an inner volume corresponding to the use which it is desired to make of the pouch. Finally, the edge 12a and the portion 12d of the edge 12'a are joined by the bottom 12e of the pouch, which is located opposite the free end 16a of the collar 16.

It has been indicated hereinabove that the weld 14 was almost continuous. In fact, as shown in FIG. 1, this weld forms a continuous line between two ends 14a and 14b between which it is interrupted. These ends are located on each side of the collar 16. In this way, the end 16a of the collar presents an opening 17 which extends over substantially the whole of its width. In the following description, it will be considered that the length of the different elements of the pouch is defined in the direction given by axis D which goes from the free end 16a of the collar to the bottom 12e of the pouch, while the width of the different elements is defined transversely to this length.

The pouch comprises a reinforcing element 22 constituted by a relatively rigid and flexible sleeve which is disposed inside the pouch, in the region of the collar 16. More precisely, this sleeve extends in the collar from a first end 22a disposed in the vicinity of the opening 17, up to a second end 22b which is located inside this pouch, in the region of the widened part 18. In the vicinity of the base 16b of the collar 16 (i.e. in the vicinity of the zone of join between the collar and the widened part), this sleeve presents a cut-out 24 on either side of which are defined a first portion 23a and a second portion 23b. Portion 23a extends between the cut-out 24 and the end 22a of the sleeve, while portion 23b extends between the cut-out and the end 22b.

The second portion 23b is provided with two tabs 26 substantially transverse to axis D. In the flattened position of the pouch, the two tabs 26 are disposed against each other, which explains why only one is visible in FIG. 1. On the other hand, in FIG. 2, the two tabs 26 are visible. The lateral ends 26a of the tabs are free, i.e. these ends do not join and are not fixed together. In this way, the cut-out 24 comprises two notches 24a and 24b which are substantially transverse and, possibly, a line of cut separating the ends 26a of the two tabs.

The sleeve is fixed inside the pouch and, as may be seen in FIG. 1, it is fixed in the region of the collar with the aid of two transverse welds 15a and 15b.

The first portion 23a of the sleeve extends over substantially the whole width of the collar 16, i.e. the distance which, in the flattened configuration, separates the longitudinal edges 22c and 22d of the sleeve in its first portion, is substantially equal to the width of the collar given by the distance between the ends 14a and 14b of the weld 14. The second portion extends overall in the extension of the first, towards the bottom 12e of the pouch. However, as has been indicated in dashed and dotted lines in FIG. 1, the maximum transverse dimension d of the second portion in the region of the tabs may be greater than the current width of the first portion. This arrangement aims at further increasing the effect of the tabs which is to space apart the two walls of the pouch in the region located below the collar.

Figure 2:
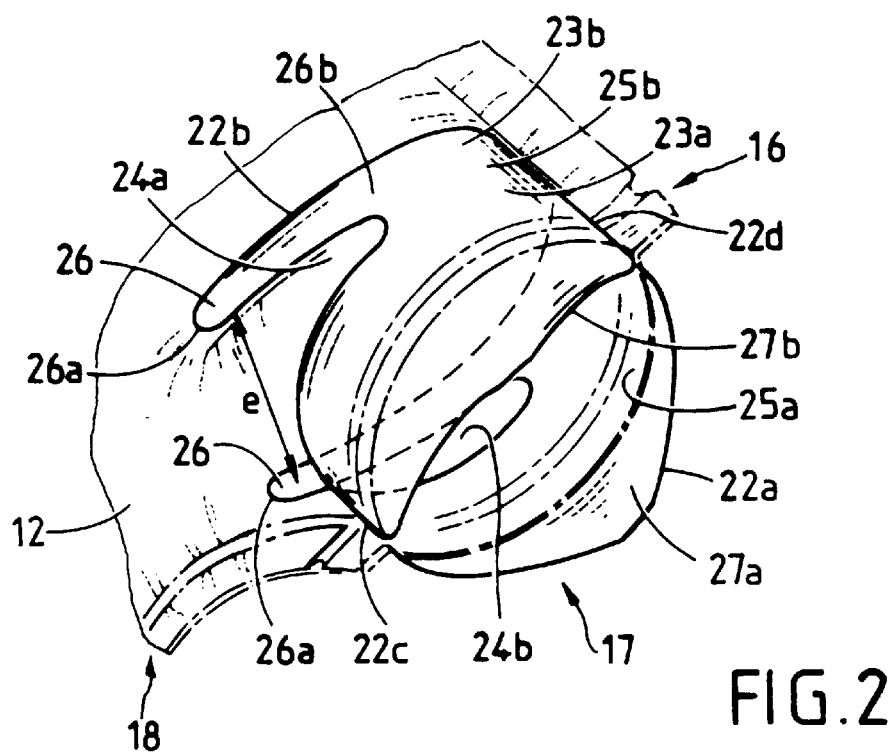
FIG. 2 is a view in perspective in the direction of arrow II of FIG. 1, showing the upper end of the pouch in its open configuration.

In fact, FIG. 2 shows the upper part of the pouch in the open configuration of the latter. In order to arrive at this configuration, the sleeve is elastically deformed so that its first portion 23a adopts a substantially tubular configuration. On the other hand, thanks to the cut-out 24 and to the fact that the lateral ends of the tabs are free, the latter remain substantially rectilinear. They are joined to the current part of the sleeve by their inner ends 26b opposite the ends 26a. When the sleeve is deformed as in FIG. 2, the inner ends 26b take a given spacing, as a function of the diameter of the first portion of the sleeve. The tabs 26 in that case conserve, over virtually the whole of their length, a spacing e substantially equal to the spacing between their respective inner ends.

In this way, when the sleeve is deformed, the collar 16 of the pouch which is disposed around the first portion 23a of the sleeve adopts a tubular form whose diameter is determined by the maximum spacing of the walls opposite the sleeve. The tabs 26 extend in the widened part 18 of the pouch and tend to move this latter apart which, in a plane perpendicular to that of FIG. 1 passing through axis D, substantially adopts the diameter of the first portion 23a of the sleeve and which, in the region of the ends of the tabs 26 (region which is remote from axis D) adopts the spacing e. In this way, the walls of the pouch separate from one another in the region of the widened part.

In the example shown, the widened part 18 is obtained by arranging for the portion 12c of the edge 12'a to move apart from edge 12a. Under these conditions, it is advantageous if the tabs are directed towards this portion 12c.

If the widened portion had another conformation, for example a truncated shape symmetrical with respect to axis D, it may be chosen to produce a sleeve similar to that of FIG. 1, directing its tabs towards one or the other of the two edges of the truncated portion. It may also be chosen to use a sleeve comprising four tabs similar to tabs 26, respectively disposed on either side of axis D so as to space apart the walls of the pouch in the widened part, in two opposite directions starting transversely to axis D.

The first portion 23a of the sleeve presents, overall, a symmetry with respect to axis D. In particular, in the open configuration, this axis corresponds to the geometrical axis of the tube that the first portion 23a of the sleeve forms. Under these conditions, the diameter of this tube is given by the spacing of the two opposite walls of the sleeve, measured along a plane passing through axis D and perpendicular to the plane of the pouch in its flattened configuration. The spacing e of the ends of the tabs is advantageously arranged to be substantially equal to this diameter. To that end, as shown in FIG. 1, the cut-out which forms the two tabs extends substantially up to axis D from a longitudinal edge 22c that the sleeve presents in its flattened configuration. In the example shown, this edge 22c is that of the longitudinal edges of the sleeve which is adjacent the portion 12c of the edge of the pouch.

Preferably, it is even desirable that this cut-out extends, in the direction going from edge 22c to the opposite edge 22d, beyond axis D. In this way, the ends 26b of the tabs are joined to the current part of the sleeve in a region on which the walls of the sleeve diverge in open configuration, i.e. they move apart from one another when the sleeve is opened. The tabs being relatively rigid, they thus tend to move apart when the sleeve is opened, following the divergent direction given by the walls of the sleeve in the region of their inner ends 26b. In this way, even if the walls of the pouch tend to resist somewhat the spacing part of the tabs 26, the spacing e between the ends 26a of these tabs is sure to be sufficient. However, for the tabs to have the desired rigidity, it is preferable if the cut-out 24 does not extend too far beyond axis D, but exceeds it only by a few millimeters.

Figure 3:
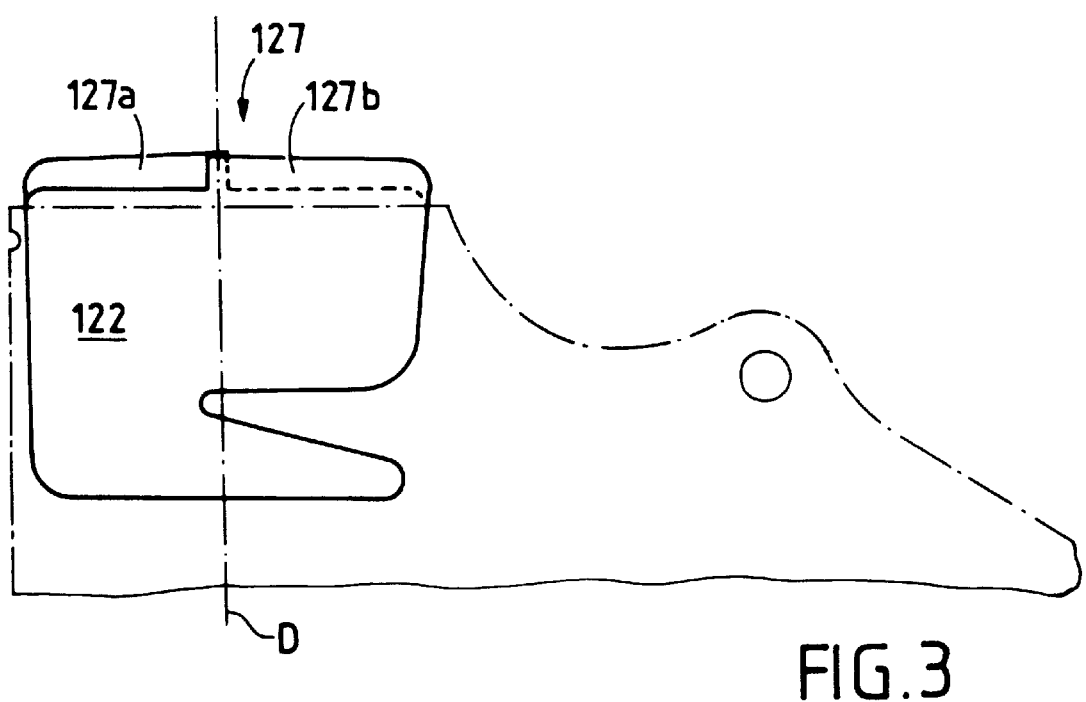
FIG. 3 is a partial view in elevation of the upper end of the pouch, in the flattened configuration, in a variant embodiment of the sleeve.

According to the example shown in FIGS. 1 to 3, the sleeve comprises two similar plates 25a and 25b which respectively constitute the first and second wall elements that the sleeve presents in its flattened configuration. These plates are naturally flat and are made of light cardboard or relatively rigid and flexible plastic. The plates are respectively fixed (for example by adhesion or by welding) on the inner faces of the pouch which are located opposite each other when the pouch occupies its flattened configuration. The plates are fixed so that their longitudinal ends are adjacent in two's and respectively close to the two longitudinal edges which the collar 16 presents when the pouch is in the flattened configuration. In this way, the two longitudinal edges of the plates respectively define the edges 22c and 22d of the sleeve previously mentioned and are not designated by other references.

In order to form the cut-out 24, each plate presents a substantially transverse notch 24a and 24b respectively. For each plate, a first and a second portion are distinguished, which respectively extend on either side of this notch and which respectively correspond to the first and second portions of the sleeve. It should be noted that another cut-out rendering the lateral ends of the tabs free is not necessary insofar as these ends normally coincide with the longitudinal edges of the plates which are initially separated from one another and are simply maintained in position thanks to the fact that the width of the first portions of the plates is substantially equal to that of the collar.

The two tabs are constituted by those portions of the plates located between their respective cut-out and that of their ends which is directed towards the inside of the pouch. Each plate presents two longitudinal edges which are respectively located in the vicinity of the two longitudinal edges that the collar presents when the pouch is in its flattened configuration.

As may be seen in the drawings, the lateral ends 26a of the tabs are rounded in order to avoid damaging the walls of the pouch when they are spaced apart.

It will also be noted that the upper edges 26c of the tabs, i.e. those edges which re turned towards the opening of the pouch, are not quite transverse but are slightly inclined so as to extend substantially parallel to the widened portion of the outer envelope of the pouch, more precisely to its edge 12c. Consequently, the tabs present a shape adapted to that of the widened portion of the pouch in which they are located and open the latter without difficulty.

The cut-out 24 is located in the vicinity of the base of the collar 16 and preferably slightly below this base in the direction towards the bottom 12e of the pouch.

It is seen in the Figures that the sleeve 22 comprises an extension 27 which extends outwardly beyond the opening 17. This extension is provided with means facilitating passage from the flattened configuration of the sleeve to its tubular configuration. These are gripping means which make it possible to grip the opposite walls of the sleeve to move them apart slightly while bringing together the longitudinal edges 22c and 22d. In the example of FIGS. 1 and 2, these gripping means are simply constituted by two tongues 27a and 27b which respectively equip the two walls of the sleeve parallel to the two opposite walls of the pouch.

FIG. 3 shows a variant embodiment in which, to simplify the drawing, the contour of the envelope is simply indicated by dashed and dotted lines. It is seen that the extension 127 of the sleeve 122 presents two tongues 127a and 127b respectively, which, contrary to the example of FIG. 2, do not have the same shape. In fact, these two tongues present two offset gripping surfaces. To produce these surfaces, it suffices to cut out the extension 127 of each of the two wall elements of the sleeve or of each of its two opposite walls, asymmetrically with respect to axis D. In this way, a cut-out portion of the extension of the first plate is opposite a solid portion of the extension of the second plate.

Figure 4:
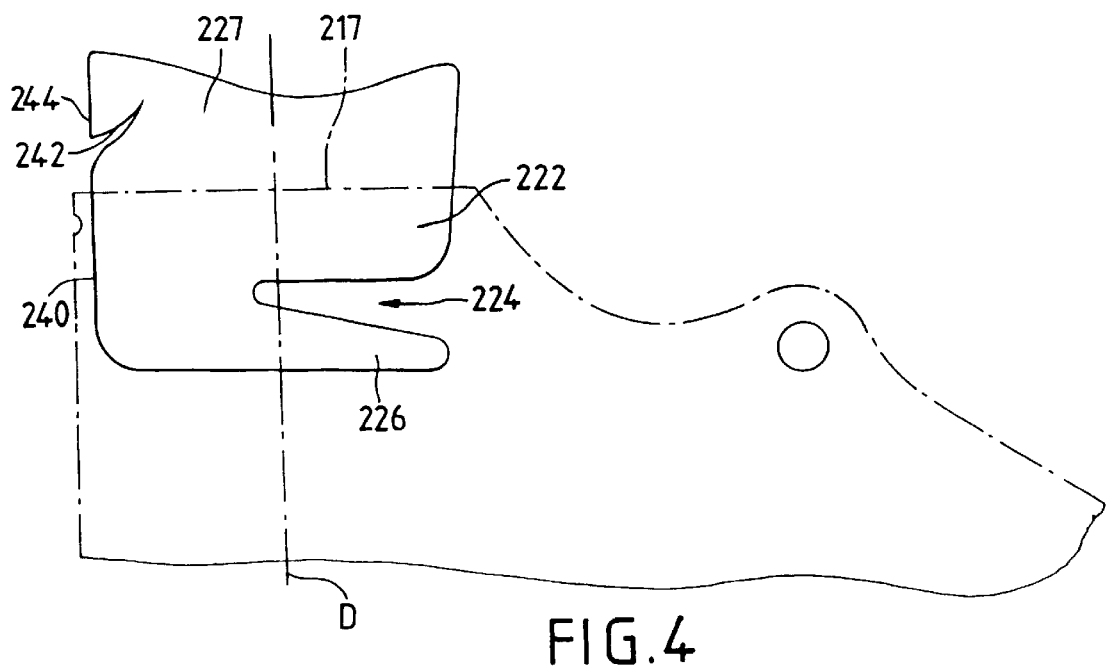
FIG. 4 is a view similar to FIG. 3, showing another variant.
Figure 5:
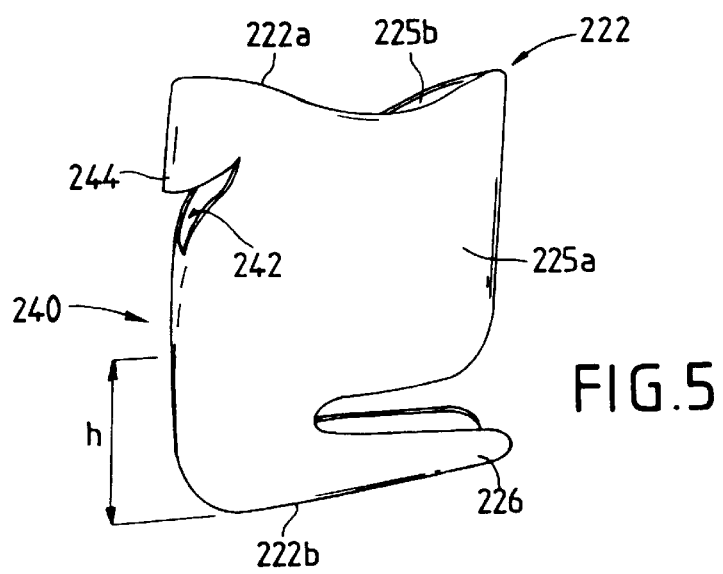
FIGS. 5 and 6 are views in perspective showing the sleeve of the variant of FIG. 4 substantially in its flattened configuration and in the open configuration, respectively.
Figure 6:
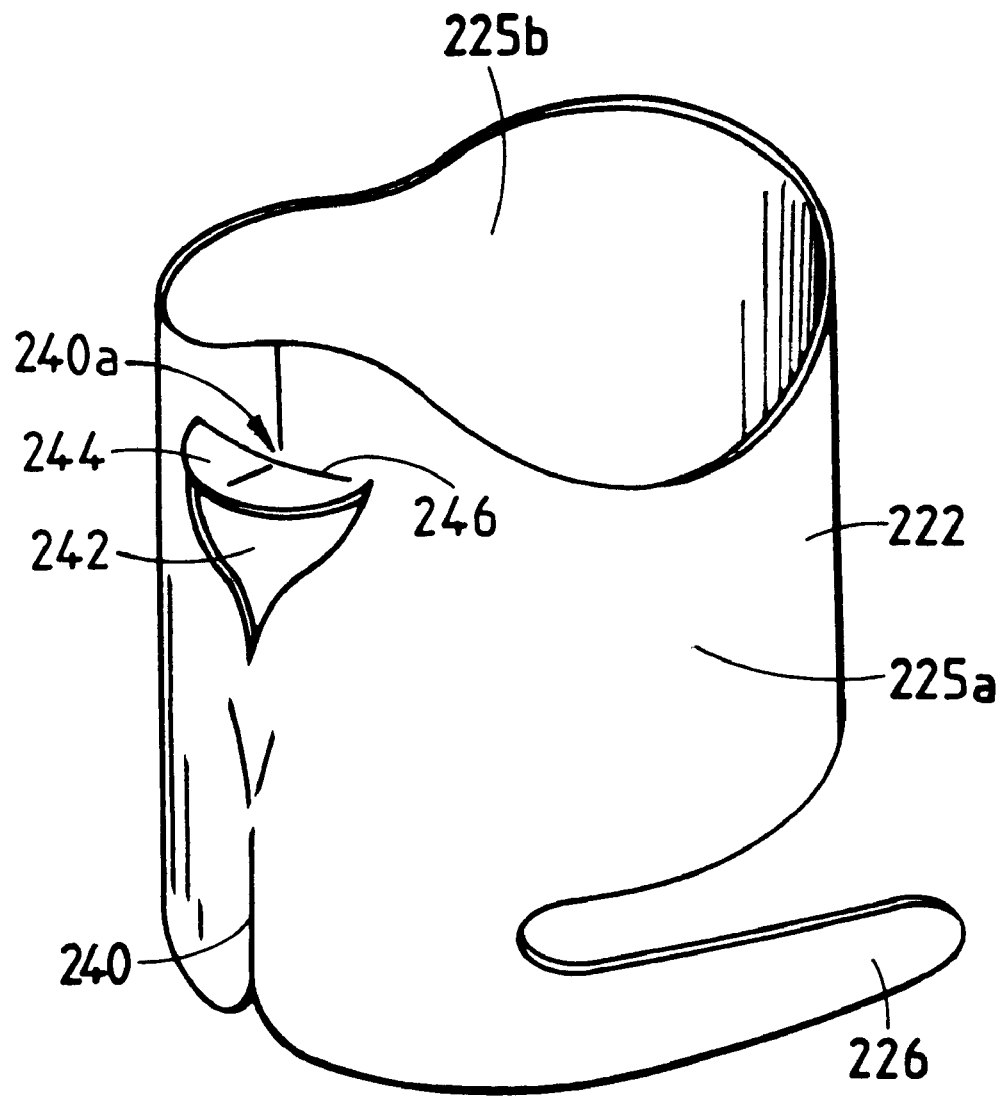

In FIGS. 4 to 6, to designate the elements common to FIGS. 1 and 2, the same references as in these Figures have been used, increased by 200. The sleeve 222 comprises a member for maintaining in open configuration.

More precisely, the sleeve presents a zone of fold 240, better visible in FIG. 5, on either side of which extend its two wall elements 225a and 225b. A cut-out 242 is formed in the sleeve and extends on either side of the zone of fold, advantageously symmetrically with respect thereto. This cut-out 242 leaves a tongue 244 which, as shown in FIG. 6, may be folded on itself. In this situation, the line of fold 246 of the tongue extends substantially transversely to the zone of fold 240 and to some extent breaks the continuity of this zone of fold, which prevents the two wall elements 225a and 225b from folding down against each other. The tongue 244, once it is folded as shown in FIG. 6, therefore holds the sleeve in its open configuration.

The tongue 244 remains in its folded position thanks to the relative rigidity of the material which constitutes the sleeve and to the hard point formed by the break 240a of the zone of fold 240.

The cut-out 242 may for example present substantially the shape of a "V", as in the Figures, that of an upturned "V", or another shape of the same type.

In FIG. 6, the tongue 244 is located in the extension 227 of the sleeve which extends outwardly beyond the opening 217, this making it possible to fold this tongue outwardly of the sleeve. However, it is possible to choose to fold it inwardly of the sleeve, and it may be located in that part of the sleeve extending in the pouch.

In the example shown, the tongue 244 is disposed in the region of the sleeve opposite the free ends of the tabs 226.

In the example of FIGS. 4 to 6, the sleeve is made in one piece and is formed in a plate which is folded on itself along a zone of fold 240. As is more readily seen in FIG. 5, it may be chosen to crush the zone of fold 240 to form a veritable fold only over a height h from the second end 222b of the sleeve, which facilitates passage of the sleeve from the flattened configuration to the open configuration.

When the pouch is intended to be used as urinal, the upper part 27, 127 or 227 of the sleeve may be shaped so as to adapt to the user's (male or female) genitals, it being possible to provide an additional piece for fit.

For use by men, the shape of the first end 22a or 222a is of little importance; it suffices that the tubular part of the sleeve in the open configuration thereof presents a sufficient diameter.

For use by women, as shown in FIGS. 4 to 6, it is preferable if the first end 222a of the sleeve presents a concave edge, symmetrical with respect to the plane of flattening of the sleeve. In this way, for use of the pouch, the edge of the sleeve may be spaced apart so as to clear the urethral meatus, optimally adapting itself to the shape of the user's genitals, without risk of leakage when urine is passed.

As shown in FIG. 1, the pouch may comprise a safety flap means, for example constituted by a plurality of inner foils disposed against each of the walls of the pouch. In the example shown, this flap means thus comprises, for each wall of the pouch, a first pair of foils 30 which extends from the opening up to a median region of the pouch. The flap means also comprises a second pair of foils 32 which extends inside the pair 30, likewise from the opening, over a length slightly less than that of the pair 30. Pair of foils 30 and pair of foils 32 are welded together by regularly spaced apart weld spots 31. Finally, the flap means comprises a third pair of foils 34 which extends inside the pair 32 over a length even shorter than that of pair 32 and which is welded to pairs 30 and 32 by weld spots 33 which are regularly spaced apart and offset with respect to the weld spots 31.

In this case, the "inner wall" of the pouch is defined, in the region of the collar, by the opposite inner faces of the two foils of the innermost pair 34. The sleeve is therefore in contact with these inner faces. Thus, the first (or the second) foils of each pair 30, 32, 34 are "sandwiched" between a first (or a second) wall of the sleeve (plate 25a or 25b) and a first (or a second) wall of the outer envelope 12. The welds 15a and 15b therefore weld together, on each side of the pouch, a wall of the sleeve, a foil of each pair 30, 32, 34 and a wall of the envelope 12.

Of course, the pouch provided with the sleeve according to the invention may comprise a different safety flap means or, depending on the applications desired, may not comprise flap means.

What is claimed is:

1. A pouch having a supple outer envelope, comprising a collar followed by a widened part, the collar having a base joined to the widened part, the collar having a free end provided with an opening, the pouch being capable of adopting a flattened configuration in which the opening is closed, while the collar is capable of adopting a substantially tubular configuration in which the opening is open, the pouch further being provided with a reinforcing element disposed adjacent to the free end of the collar, the reinforcing element comprising a relatively rigid and flexible sleeve disposed inside the pouch, the sleeve extending in the collar from a first end located adjacent to the opening, and extending to a second end located towards the widened part;

the sleeve having adjacent the base of the collar joined to the widened part, a cut-out on either side of which are defined a first portion located towards the first end of the sleeve and a second portion located towards the second end of said sleeve, the second portion being provided with at least two substantially transverse tabs which face each other and which have free lateral ends; and further wherein in the flattened configuration of the pouch, the sleeve is flattened and presents two wall elements disposed one against the other, and in order to bring the collar into its substantially tubular configuration and open the opening, the sleeve is capable of being elastically deformed in order to have an open configuration, in which the first portion is substantially tubular, while the lateral ends of the tabs are spaced apart from one another.

2. The pouch of claim 1, wherein, the first portion of the sleeve has a longitudinal axis of symmetry, the cut-out forming the two tabs extending at least substantially up to the axis of symmetry from a longitudinal edge that the sleeve has in its flattened configuration.

3. The pouch of claim 1, wherein the sleeve comprises a member adapted to maintain said sleeve in the open configuration and capable of being formed to place the sleeve in the open configuration.

4. The pouch of claim 3, wherein the sleeve presents a zone of fold which joins said two wall elements of the sleeve and the sleeve has a tongue formed by a cut-out extending on either side of said zone of fold, the tongue being capable of being folded on itself.

5. The pouch of claim 4, wherein the tongue extends in a region of the sleeve opposite the free ends of the tabs.

6. The pouch of claim 1, wherein the sleeve is formed by a plate folded on itself along a zone of fold on either side of which extend the two wall elements of the sleeve.

7. The pouch of claim 1, wherein the sleeve comprises two similar plates fixed inside the pouch, respectively on two opposite inner faces of the pouch, each plate presenting a substantially transverse notch on either side of which extend a first and a second portion corresponding respectively to the first and second portions of the sleeve, each plate presenting two longitudinal edges respectively located in the vicinity of a first and a second longitudinal edge that the collar presents when the pouch is in its flattened configuration.

8. The pouch of claim 1, wherein the tabs have edges which face the opening, said edges being substantially parallel to the widened portion of the outer envelope of the pouch.

9. The pouch of claim 1, wherein the sleeve comprises an extension extending outwardly beyond the opening, the extension being provided with means for facilitating passage from the flattened configuration to the open configuration.

10. The pouch of claim 9, wherein the sleeve comprises a member adapted to maintain said sleeve in the open configuration and capable of being formed to place the sleeve in the open configuration and further wherein said member is located in said extension.

11. The pouch of claim 9, wherein the sleeve has a zone of fold which joins said two wall elements of the sleeve, wherein the sleeve presents a tongue formed by a cut-out extending on either side of said zone of fold, the tongue being capable of being folded on itself and wherein the tongue is located in said extension.

* * * * *